(12) United States Patent
Overbeck et al.

(10) Patent No.: US 7,545,499 B2
(45) Date of Patent: Jun. 9, 2009

(54) SYSTEMS AND METHODS FOR MEASURING A COLORED FLEXIBLE MATERIAL DURING A MANUFACTURING PROCESS

(75) Inventors: James L. Overbeck, Ada, MI (US); Richard J. Van Andel, Grand Rapids, MI (US)

(73) Assignee: X-Rite, Inc., Grand Rapids, MI (US)

( * ) Notice: Subject to any disclaimer, the term of this patent is extended or adjusted under 35 U.S.C. 154(b) by 345 days.

(21) Appl. No.: 11/402,788

(22) Filed: Apr. 12, 2006

(65) Prior Publication Data

US 2006/0244935 A1 Nov. 2, 2006

Related U.S. Application Data

(60) Provisional application No. 60/670,407, filed on Apr. 12, 2005.

(51) Int. Cl.
*G01N 21/84* (2006.01)
(52) U.S. Cl. ...................... 356/429; 356/402
(58) Field of Classification Search ................. 356/429, 356/430, 431, 402, 416
See application file for complete search history.

(56) References Cited

U.S. PATENT DOCUMENTS

| | | | |
|---|---|---|---|
| 4,413,276 A | 11/1983 | Hertz et al. | |
| 4,558,786 A | 12/1985 | Lane | |
| 4,566,797 A | 1/1986 | Kaffka et al. | |
| 4,618,257 A | 10/1986 | Bayne et al. | |
| 4,707,838 A | 11/1987 | Reule et al. | |
| 4,797,609 A | 1/1989 | Yang | |
| 4,988,875 A * | 1/1991 | Ortiz et al. | 250/330 |
| 5,072,128 A | 12/1991 | Hayano et al. | |
| 5,128,753 A * | 7/1992 | Lemelson | 382/141 |
| 5,132,736 A | 7/1992 | Muramatsu et al. | |
| 5,137,364 A | 8/1992 | McCarthy | |
| 5,258,858 A * | 11/1993 | Chow | 358/484 |
| 5,311,293 A | 5/1994 | MacFarlane et al. | |
| 5,313,267 A | 5/1994 | MacFarlane et al. | |
| 5,471,052 A | 11/1995 | Ryczek | |
| 5,544,090 A * | 8/1996 | Shofner et al. | 702/82 |
| 5,634,171 A * | 5/1997 | Muto | 399/32 |

(Continued)

FOREIGN PATENT DOCUMENTS

EP 0117606 A1 9/1984

(Continued)

OTHER PUBLICATIONS

U.S. Appl. No. 11/504,187, filed Aug. 15, 2006 (22 pages).

(Continued)

*Primary Examiner*—Roy Punnoose
(74) *Attorney, Agent, or Firm*—McCarter & English, LLP (57) ABSTRACT

A method for measuring a flexible colored material during a manufacturing process. The method includes automatically diverting the flexible material from a process path, placing the flexible material in contact with a rotatable drum, and measuring spectral data of the flexible material as the drum rotates. Measuring the spectral data includes scanning the flexible material with a line scanning detector having an array of detectors. The method also includes processing scan information to form a single image of the flexible material.

20 Claims, 5 Drawing Sheets

U.S. PATENT DOCUMENTS

| | | | |
|---|---|---|---|
| 5,671,735 A | 9/1997 | MacFarlane et al. | |
| 5,838,451 A | 11/1998 | McCarthy | |
| 5,844,680 A | 12/1998 | Sperling | |
| 5,854,680 A | 12/1998 | Rakitsch | |
| 5,917,183 A | 6/1999 | Sperling | |
| 6,020,583 A | 2/2000 | Walowit et al. | |
| 6,067,504 A | 5/2000 | MacFarlane et al. | |
| 6,129,664 A | 10/2000 | Macfarlane et al. | |
| 6,147,761 A | 11/2000 | Walowit et al. | |
| 6,157,445 A | 12/2000 | Macfarlane et al. | |
| 6,178,341 B1 | 1/2001 | Macfarlane et al. | |
| 6,271,920 B1 | 8/2001 | Macfarlane et al. | |
| 6,278,477 B1 * | 8/2001 | Ohba | 347/251 |
| 6,308,088 B1 | 10/2001 | MacFarlane et al. | |
| 6,314,372 B1 | 11/2001 | Macfarlane et al. | |
| 6,330,341 B1 | 12/2001 | Macfarlane et al. | |
| 6,384,918 B1 | 5/2002 | Hubble, III et al. | |
| 6,400,099 B1 | 6/2002 | Walker | |
| 6,556,932 B1 | 4/2003 | Mestha et al. | |
| 6,577,395 B1 | 6/2003 | Berns et al. | |
| 6,584,435 B2 | 6/2003 | Mestha et al. | |
| 6,587,793 B2 | 7/2003 | Viassolo et al. | |
| 6,621,576 B2 | 9/2003 | Tandon et al. | |
| 6,653,992 B1 | 11/2003 | Colbeth et al. | |
| 6,661,513 B1 | 12/2003 | Granger | |
| 6,690,471 B2 | 2/2004 | Tandon et al. | |
| 6,721,692 B2 | 4/2004 | Mestha et al. | |
| 6,732,917 B1 | 5/2004 | Benz et al. | |
| 6,760,124 B1 | 7/2004 | Boerger et al. | |
| 6,765,674 B2 | 7/2004 | Orelli et al. | |
| 6,844,931 B2 | 1/2005 | Ehbets | |
| 6,903,813 B2 | 6/2005 | Jung et al. | |
| 6,958,810 B2 | 10/2005 | Jung et al. | |
| 7,027,186 B2 | 4/2006 | Sano et al. | |
| 7,057,727 B2 | 6/2006 | Ott | |
| 7,113,281 B2 | 9/2006 | Ott | |
| 2003/0098896 A1 | 5/2003 | Berns et al. | |
| 2004/0208210 A1 | 10/2004 | Inoguchi | |
| 2005/0036163 A1 | 2/2005 | Edge | |
| 2006/0244806 A1 | 11/2006 | Overbeck et al. | |
| 2006/0244948 A1 | 11/2006 | Overbeck | |
| 2006/0244960 A1 | 11/2006 | Overbeck et al. | |
| 2007/0035740 A1 | 2/2007 | Nisper et al. | |

FOREIGN PATENT DOCUMENTS

| | | |
|---|---|---|
| EP | 0292957 B1 | 4/1991 |
| EP | 0642012 A1 | 3/1995 |
| EP | 0871025 A1 | 10/1998 |
| EP | 0696867 B1 | 3/2000 |
| EP | 1001393 A2 | 5/2000 |
| EP | 1291628 A2 | 3/2003 |
| EP | 1293762 A2 | 3/2003 |
| EP | 1326199 A2 | 7/2003 |
| EP | 0936400 B1 | 3/2006 |
| GB | 1589335 A | 5/1981 |
| JP | 59060324 A | 4/1984 |
| JP | 2003185591 A | 7/2003 |
| WO | WO 98/11410 A1 | 3/1998 |
| WO | WO 00/16045 A1 | 3/2000 |
| WO | WO 01/016990 A1 | 3/2001 |
| WO | WO 03/007663 A1 | 1/2003 |
| WO | WO 03/083765 A1 | 10/2003 |
| WO | WO 2004/056135 A1 | 7/2004 |
| WO | WO 2005/013365 A2 | 2/2005 |
| WO | WO 2005/050148 A2 | 6/2005 |
| WO | WO 2005/114118 A1 | 12/2005 |
| WO | WO 2006/020833 A2 | 2/2006 |
| WO | WO 2006/053808 A1 | 5/2006 |

OTHER PUBLICATIONS

International Search Report for PCT/US06/12416, Jan. 25, 2007 (4 pages).

International Search Report for PCT/US2006/031891, Feb. 5, 2007 (8 pages).

International Search Report for PCT/US2006/031892, Feb. 16, 2007 (8 pages).

James H. Nobbs, "Colour-Match Prediction for Pigmented Materials," from *Colour Physics for Industry*, Chapter 6, pp. 292-372, (Roderick McDonald ed., Society of Dyers and Colourists, 2d ed. 1997).

Gunter Wyszecki & W.S. Stiles, *Color Science: Concepts and Methods, Quantitative Data and Formulae*, pp. 221-222, 785-86, (Joseph W. Goodman ed., John Wiley & Sons, Inc., 2d. ed. 1982).

Rolf G. Kuehni, Verona Division of Mobay Chemical Corp., *Computer Colorent Formulation*, Chapters 3-6, pp. 11-86, (Lexington Books 1975).

Paul Henry Hoffenberg, Automated Color-Matching of Printed Ink films (1972) (unpublished Ph.D. dissertation, Lehigh University) (on file with UMI Dissertation Information Service).

Raja Balasubramanian, *Optimization of the Spectral Neugebauer Model for Printer Characterization*, 8 Journal of electronic Imaging 156, 156-166 (1999).

Henry R. Kang, *Applications of Color Mixing Models to electronic Printing*, 3 Journal of Electronic Imaging 276, 276-87 (1994).

R.D. Hersch et al., *Spectral Prediction and Dot Surface Estimation Models for Halftone Prints*, 5293 SPIE 356, 356-69 (2004).

Safer Mourad, Color Predicting Model for Electrophotographic Prints on Common Office Paper (2003) (unpublished M.S. thesis, Swiss Federal Institute of Technology), at htt://diwww.epfl.ch/w31sp/pub/papers/colour/thesis-mourad.pdf.

International Search Report, Aug. 9, 2007.

E.J. Neugebauer, *Die Theoretischen Grundlagen des Mehrfarbenbechdrucks* (*The Theoretical Foundation for Multicolor Printing*), 36(4), pp. 73-89, 1937. Reprinted in Neugebauer Memorial Seminar on Color Reporduction, vol. 1184 of Proceedings of the SPIE, pp. 194-202. SPIE, Bellingham, WA, 1990.

\* cited by examiner

SYSTEMS AND METHODS FOR MEASURING A COLORED FLEXIBLE MATERIAL DURING A MANUFACTURING PROCESS

CROSS-REFERENCE TO RELATED APPLICATIONS

This application claims the priority benefit of U.S. Provisional Patent Application No. 60/670,407, filed on Apr. 12, 2005.

BACKGROUND

This application discloses an invention that is related, generally and in various embodiments, to systems and methods for measuring a colored flexible material during a manufacturing process.

For printing processes such as sheet-fed lithographic printing, flexographic, ink jet, etc., it is very important to accurately monitor the output of the production equipment for quality control purposes. A common example of production equipment that produces colored flexible materials is a sheet-fed printing press. In general, as flexible sheets advance through the press, colors are applied to the flexible sheets at various printing units of the press. The colored flexible sheets may then be guided through additional paths of the production process. For example, the colored flexible sheets may be guided through coating and drying stages of the production process. Typically, the final step of the production process is to collect all of the colored flexible sheets in a delivery unit positioned at an end of the printing press. For such processes, the color of the flexible printed materials is usually monitored in one of two ways.

The first method involves having the press operator remove one of the recently printed sheets from the delivery unit, carry the sheet over to a flat surface that is often positioned on or near the press console, and lay the sheet down onto the flat surface. A color controlled light positioned above the flat surface allows the press operator to visually inspect the printed colors and to measure the sheet in either an automated or manual fashion with a spectrophotometer or densitometer. As this method requires press operator intervention, the process is not automated. In addition, the time delay between removal of the printed sheet from the delivery unit and the actual acquisition of the color data can vary considerably. Due to the ink dry back effect, the color of the printed sheets can change significantly in the first minutes after printing. Therefore, the variable time delay makes it difficult for someone using this method to accurately predict the final color of the printed sheets.

The second method is an automated method that allows for measurement of the printed sheet on the printing press. This method utilizes color measurement equipment that is integral with the printing press or one of the extra units. The printed sheets are measured at press speed, so the equipment must measure very quickly to sample a single sheet, or it must synchronize itself so that it can gather a complete dataset from many different pages. The color measurement equipment may operate in different ways. For example, the color measurement equipment may utilize flash lamps that can measure very quickly, in essence "stopping the motion" of the printing press. Alternatively, the color measurement equipment may utilize a slow scan across the printing press and synchronize the acquisition time to generate a complete dataset. This method measures the printed sheet within seconds of printing before the sheet arrives at the delivery unit. At the time of the measurement, the ink on the printed sheet will either be wet, or hot if a drying unit is used. In either the wet or dry condition, the ink color will be different from its long term "dried back" value. Although this method addresses the variable time delay problem associated with the first method, the cost of the system (i.e., the printing press system with the integral color measurement equipment) tends to be relatively expensive.

SUMMARY

In one general respect, this application discloses a method for measuring a colored flexible material during a manufacturing process. According to various embodiments, the method comprises automatically diverting the flexible material from a process path, placing the flexible material in contact with a rotatable drum, and measuring spectral data of the flexible material as the drum rotates. Measuring the spectral data comprises scanning the flexible material with a line scanning detector having an array of detectors. The method also comprises processing scan information to form a single image of the flexible material.

In another general respect, this application discloses a system for measuring a colored flexible material during a manufacturing process. According to various embodiments, the system comprises a measuring unit. The measuring unit comprises a rotatable drum, a measuring head, and a scan alignment module for aligning scan information to form an image of the colored flexible material.

Aspects of the disclosed invention may be implemented by a computer system and/or by a computer program stored on a computer readable medium. The computer readable medium may comprise a disk, a device, and/or a propagated signal.

Other features and advantages will be apparent from the following description, including the drawings, and from the claims.

DETAILED DESCRIPTION

The figures and descriptions of the disclosed invention have been simplified to illustrate elements that are relevant for a clear understanding of the disclosed invention. It should be understood that the methods, products, and systems described below may include various other processes, components, and elements in actual implementation.

Figure 1:
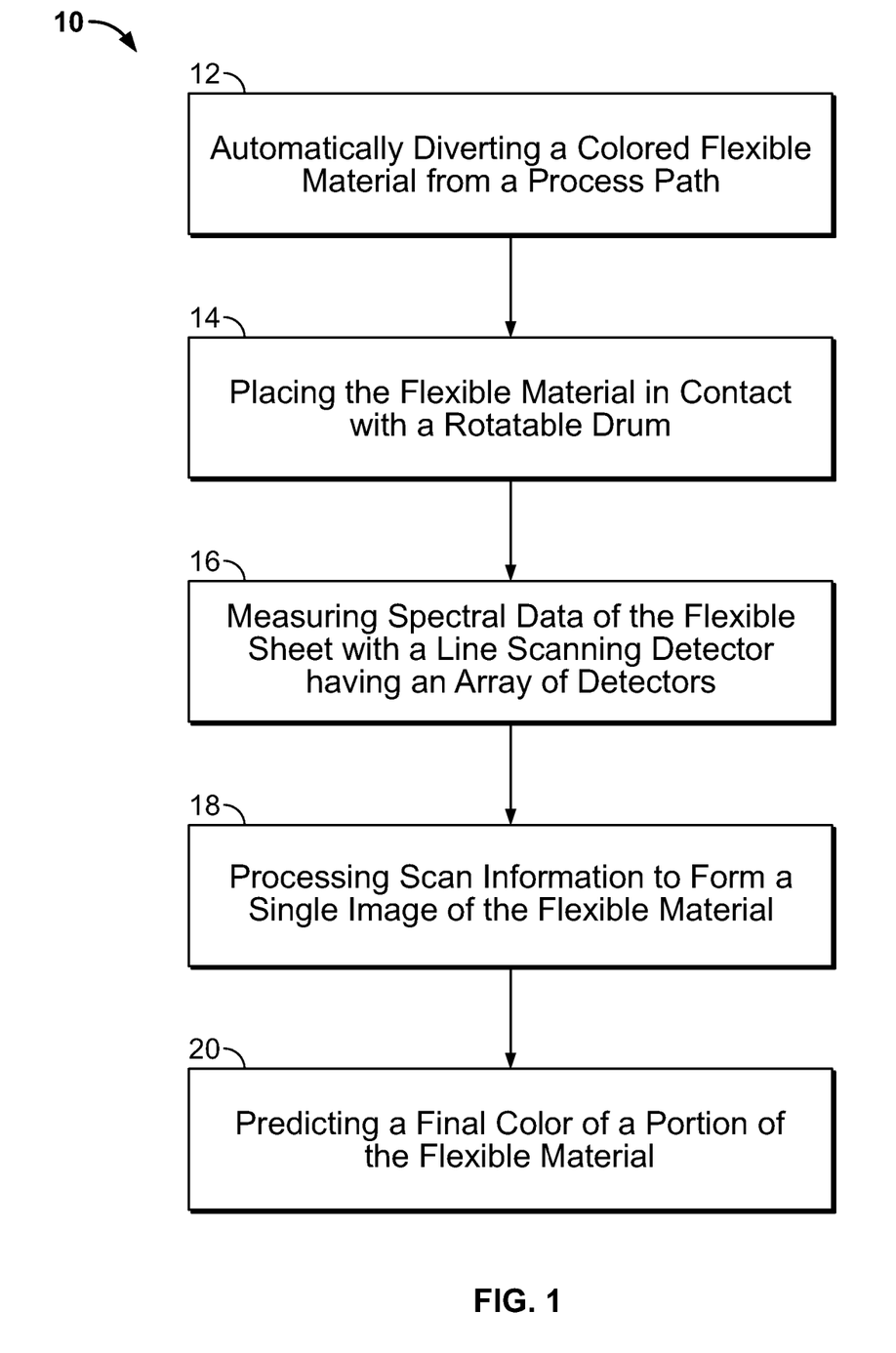
FIG. 1 illustrates various embodiments of a method for measuring a colored flexible material during a manufacturing process.

FIG. 1 illustrates various embodiments of a method 10 for measuring a colored flexible material during a manufacturing process. The manufacturing process may be any of a number of different manufacturing processes. For example, the manufacturing process may be a sheet-fed lithographic process, a flexographic printing process, an ink jet printing process, a coil coating process, etc. The colored flexible material may comprise any type of colored flexible material such as, for example, a printed sheet, a coated coil, etc. For ease of description purposes, the manufacturing process will be described in the context of a sheet-fed printing process, where the colored flexible material is a rectangular-shaped colored sheet of paper stock.

Figure 3:
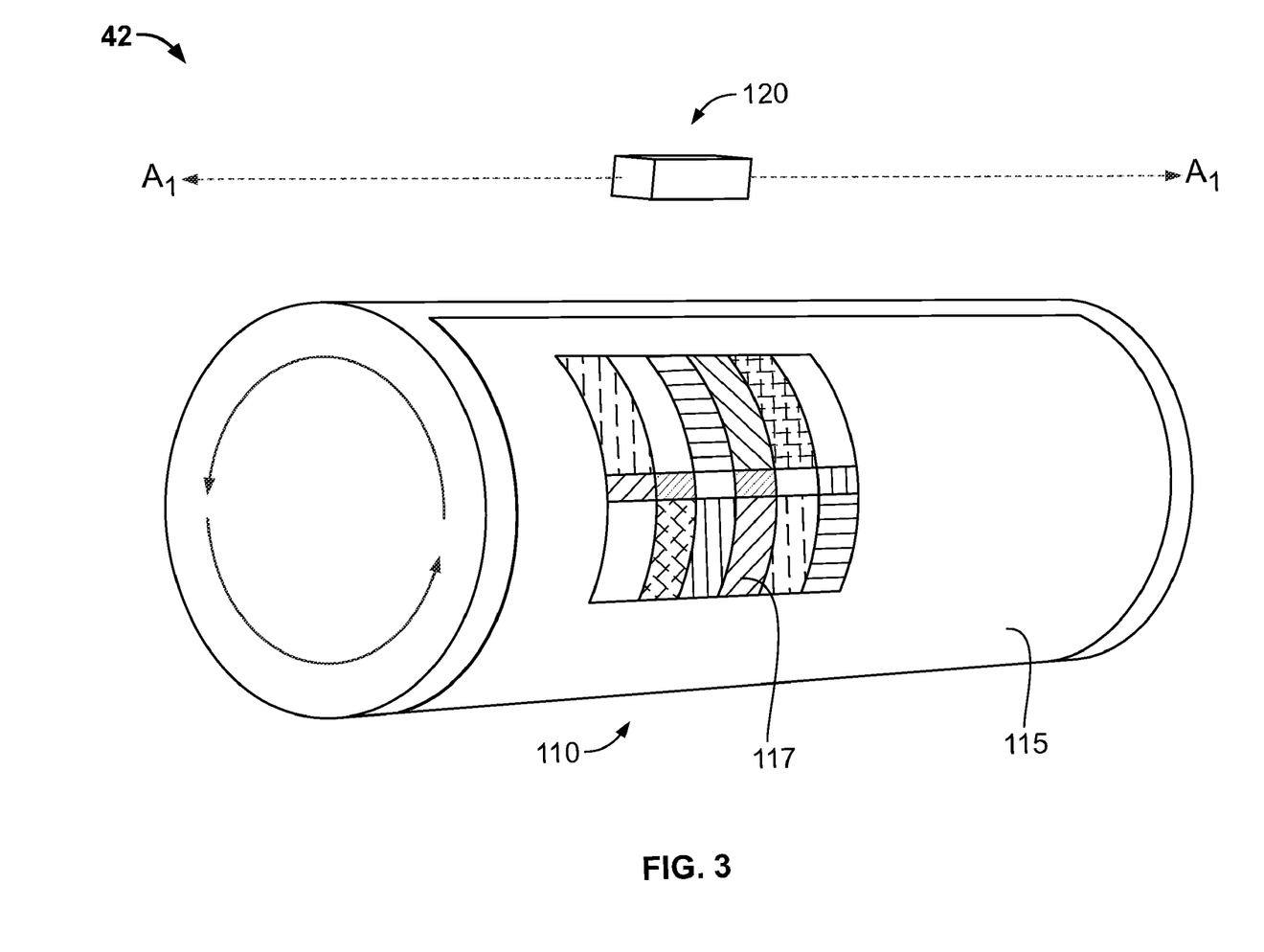
FIG. 3 illustrates an exemplary measuring unit including a rotatable drum and a line scanning detector.
Figure 4:
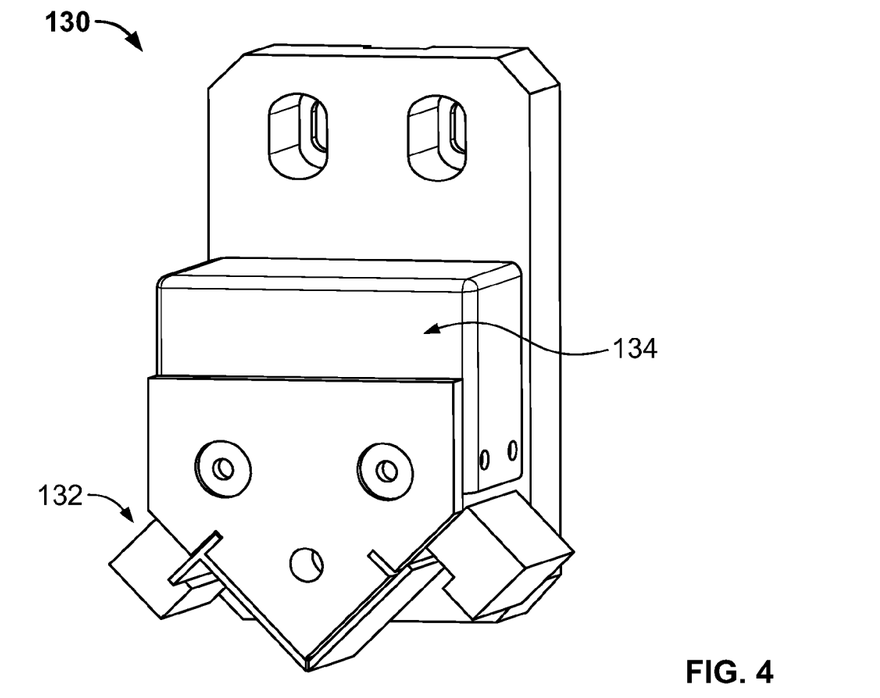
FIGS. 4 and 5 depict an exemplary measuring head for a line scanning detector including an illumination source and an array of detectors. Note that a front housing cover of the exemplary measuring head has been removed in FIG. 5 to allow viewing of internal components.
Figure 5:
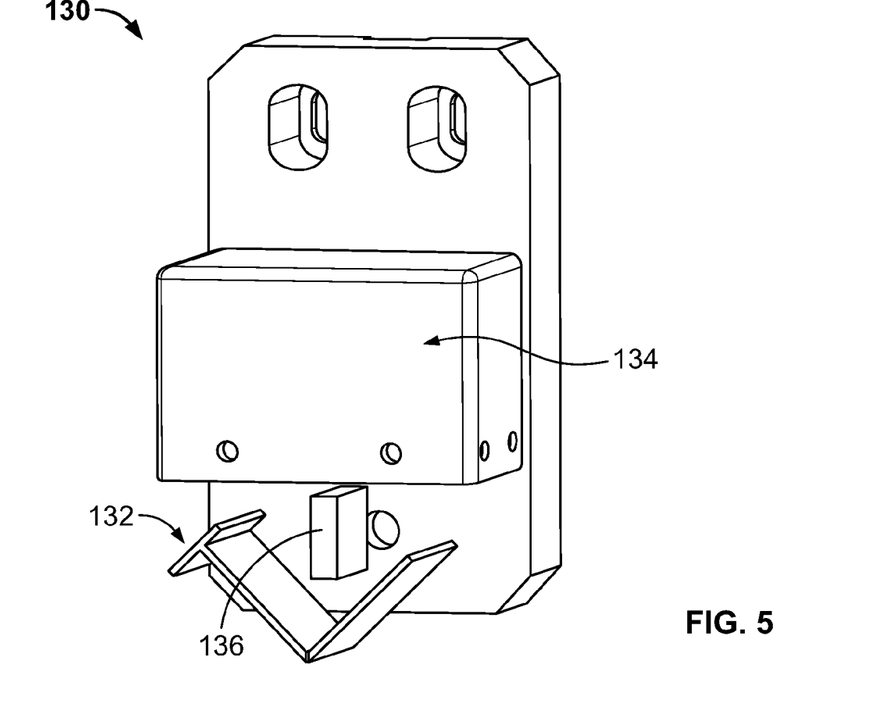

The method starts at block 12 where a colored sheet of paper stock is automatically diverted from its typical process path. For example, a typical process path for a given sheet may be to apply one or more colors to the sheet in a sequential manner, pass the colored sheet through a drying unit, then deliver the colored sheet to the delivery unit. The delivery unit may serve to collect a stack of the colored sheets. In lieu of delivering each colored sheet to the delivery unit, the method 10 may automatically divert a given colored sheet past the delivery unit to a measuring unit that is integrated with the printing press. Referring now to FIG. 3, an exemplary measuring unit 42 is depicted. The measuring unit 42 may comprise a rotatable drum 110 and one or more line scanning detectors 120. Each line scanning detector 120 may comprise a measuring head, e.g. the measuring head 130 depicted in FIGS. 4 and 5. An exemplary measuring head 130 may comprise an illumination source, e.g., an LED array 132, and an array of detectors 134. Referring to FIGS. 3-5, each line scanning detector 120 may further comprise a subsystem configured to move the measuring head 130 smoothly along a longitudinal axis $A_1$ of the drum 110. According to various embodiments, the subsystem may be configured to move the measuring head 130 in a stepping manner along the longitudinal axis $A_1$ of the drum 110. According to other embodiments, the measuring head 130 may be of a width that allows it to measure the colored sheet without having to traverse along the longitudinal axis $A_1$ of the drum 110.

Referring again to the method of FIG. 1, the colored sheet may be diverted past the delivery unit in any suitable manner. For example, when a chain delivery system is utilized to advance the colored sheets thru the drying unit to the delivery unit, each colored sheet may be releasably held in position by one or more grippers of the chain delivery system. As the colored sheets reach the delivery unit, the grippers may operate to release the colored sheets, thereby allowing the colored sheets to drop and form a stack of colored sheets. However, for the colored sheet that is to be diverted to the measuring unit, the one or more grippers releasably holding the colored sheet in position may operate to retain the colored sheet until it passes the delivery unit and approaches or reaches the measuring unit. As the colored sheet approaches or reaches the measuring unit, the one or more grippers releasably holding the colored sheet may operate to release the colored sheet. The process described at block 12 may be repeated at any frequency. For example, one out of every five-hundred colored sheets, or one out of every thousand colored sheets may be diverted from the typical process path.

From block 12, the method advances to block 14, where the diverted colored sheet is placed in contact with a rotatable drum; see, e.g., FIG. 3, wherein an exemplary color sheet 115 is depicted in contact with an exemplary drum 110. The drum may be a smooth black drum that comprises a portion of a measuring unit, and the measuring unit may have a geometry that provides a reasonably small form factor that allows the measuring unit to be placed on or near the equipment used to produce the colored sheets (e.g., the printing press). The drum geometry may also serve to maintain the colored sample at a constant distance from the measuring head. The colored sheet may be placed in contact with the drum in any suitable manner. For example, the colored sheet may be tensioned around the drum, held in contact with the drum by a vacuum, held in contact with the drum by an electrostatic charge, etc. The colored sheet may be held appropriately and firmly in contact with the drum during the measurement process. The speed of the drum may be controlled and synchronized to the printing press such that the diverted colored sheet can be placed in contact with the drum at the normal operating speed of the printing press. The drum can be rotated rapidly to accept the colored sheet at press speed, and stopped or turned slowly during the measurement operation. This flexibility allows the measuring unit to accept a diverted colored sheet, hold the colored sheet for a known period of time while the ink dries, move the colored sheet smoothly and accurately while the colored sheet is measured, and finally to allow the colored sheet to be released into a bin for measured color sheets.

From block 14, the process advances to block 16, where spectral data of the colored sheet is measured as the drum rotates. The measured spectral data may be stored in a memory. According to various embodiments, for printing processes which utilize a drying unit, the colored sheet may first be retained at the drum for a period of time until the colored sheet has sufficiently cooled. The spectral data is measured by scanning the colored sheet with one or more line scanning detectors as the drum and the colored sheet rotate. Each line scanning detector comprises a portion of the measuring unit and includes an array of detectors. For embodiments where the spectral data is measured by a plurality of line scanning detectors, each line scanning detector includes an array of detectors.

Figure 7:
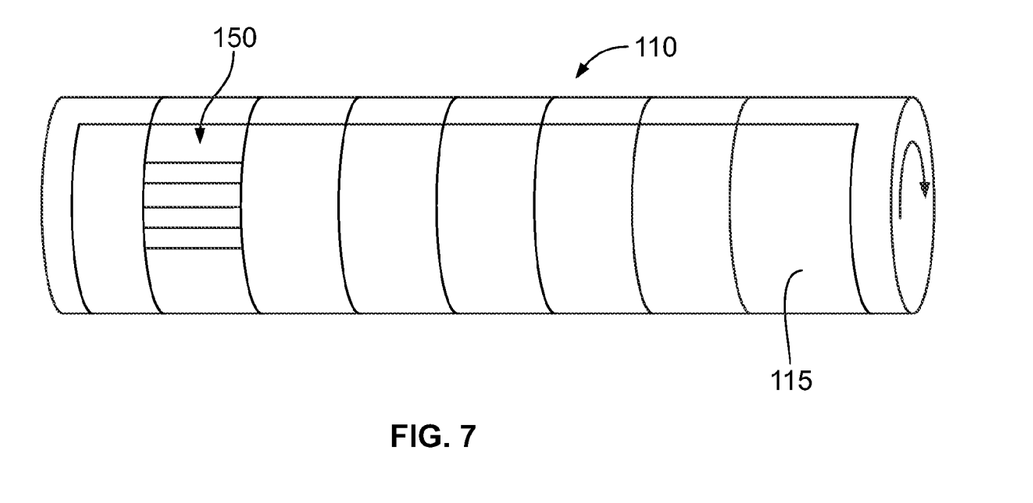

According to various embodiments, such as depicted in FIGS. 5 and 7, as the drum 110 rotates, the measuring head 130 (see FIGS. 4 and 5) projects one or more lines of light 150 onto the colored material 115, and detects one or more lines of pixels 160 across the colored sheet. When more than one line of light 150 is projected (as in the embodiment depicted in FIG. 7), the lines of light 150 are parallel lines of light. Similarly, when the measuring head 130 detects more than one line of pixels, the lines of pixels are parallel lines of pixels. Each measuring head 130 may comprise multiple optical channels and may measure multiple wavelength responses. The multiple optical channels allow the measuring head to read multiple pixels at a time which speeds the reading process. For example, each measuring head may be configured to detect one row of 1024 pixels which would allow the measuring head to cover about five inches of the colored sheet at two-hundred dots per inch. Each measuring head 130 may be configured to detect multiple rows of pixels to measure multiple wavelength responses at the same time.

According to various embodiments, the illumination source comprises a switchable narrow band light source. For example, the switchable narrow band light source may comprise a plurality of light emitting diodes (LEDs), wherein each light emitting diode emits light at a different wavelength. The plurality of LEDs may be configured as a line illuminating LED array 132, such as depicted in FIGS. 4-5. According to other embodiments, when the spectral data is measured by scanning the colored sheet with multiple line scanning detectors (see, e.g., FIG. 7), each measuring head may include a different illumination source. For such embodiments, each illumination source may comprise one or more narrow band light sources, and each narrow band light source may provide a different wavelength of light. Alternatively, each measuring head may comprise a white light source and filters on each line scanning detector. The multiple line scanning detectors may serve to increase the speed or throughput of the measuring equipment.

According to yet other embodiments, the measuring equipment may comprise a white light source, at least one dispersive element, e.g., the dispersive element 136 depicted in FIG. 5, through which light reflected from the colored sheet passes, and a two-dimensional detector. The two-dimensional detector may comprise an array of detectors. The dispersive element 136 may comprise one or more prisms, a grating, or any combination thereof The dispersive element 136 may disperse wavelengths in one dimension while the other dimension may represent the pixel location across the scan line.

Figure 6:
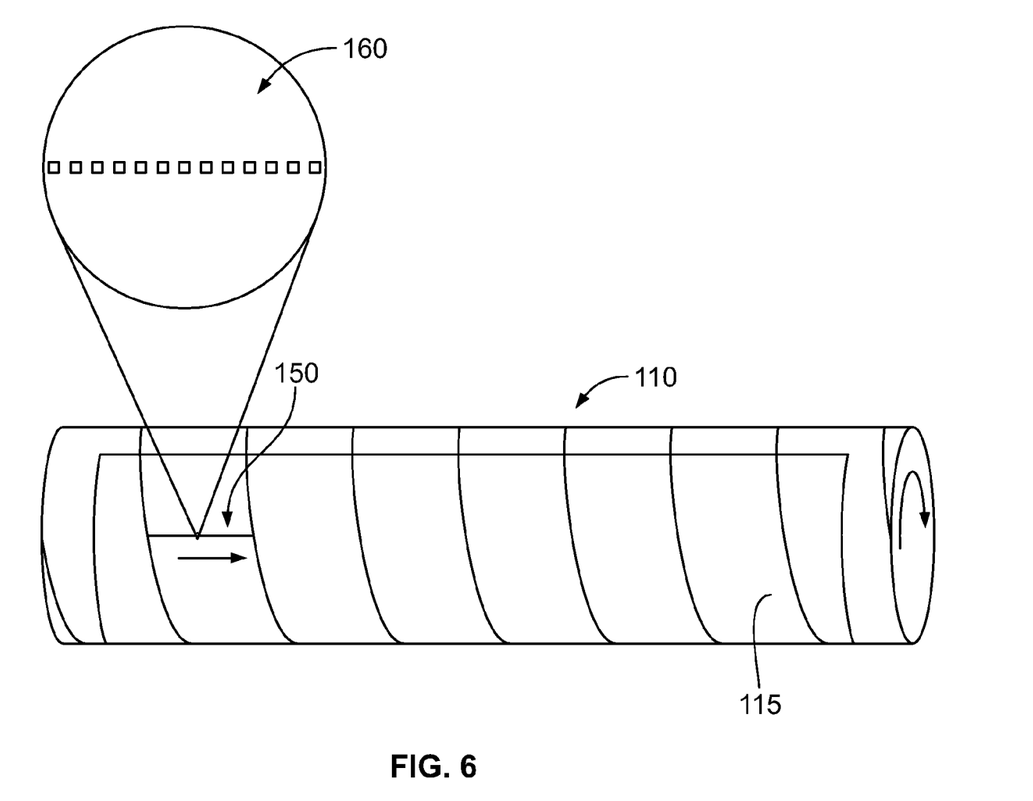
FIGS. 6 and 7 depict scan configurations for (i) a measuring unit including a line scanning detector which follows a helical-shaped path, and (ii) a measuring unit including a plurality of line scanning detectors which follows a cylindrical-shaped path.

With reference again to FIG. 3, after the diverted colored sheet 115 is loaded onto the drum 110, the one or more line scanning detectors 120 may measure the spectral data of a color bar that comprises a portion of the colored sheet 115, e.g., color bar 117 of FIG. 3. The spectral data associated with the color bar 117 may provide immediate feedback to any automated ink: control units that comprise a portion of the printing press. The one or more line scanning detectors 120 may scan the remaining portion of the colored sheet 115. As the drum 110 rotates and each scanning detector 120 moves smoothly along the longitudinal axis $A_1$ of the drum 110, helical-shaped portions of the colored sheet are scanned by the measuring head of each scanning detector 120. Referrinq now to FIG. 6, the scanned helical portions of an exemplary colored sheet 115 are depicted. The drum 110 rotates allowing for the measuring head (not depicted) to scan the helical portions of the color sheet 115. The combination of the linear and rotation motion causes the colored sheet 115 to be scanned in a manner such that there is an overlap or exact edge alignment with a previously scanned area of one or more pixels 160. According to other embodiments, based on the size and/or movement of the measuring head, the entire colored sheet 115 maybe scanned, or cylindrical subportions (see FIG. 7) of the colored sheet 115 maybe scanned as the measuring head is stepped along the longitudinal axis of the drum 110.

For embodiments utilizing multiple measuring heads, where each measuring head includes two different LED wavelength illuminators, the measuring heads may be positioned around the perimeter of the drum such that any point on the measured colored sheet will eventually pass under each measuring head. -By multiplexing the LEDs in a manner that allows the same pixel to be measured with all ten wavelengths, each pixel on the colored sheet may be measured by ten different LED bands. The ten LED bands may comprise, for example, nine spectral bands from 400 nm through 700 nm and one additional band in the near infra-red.

Referring again to FIG. 1, from block 16, the method advances to block 18, where the scan information generated at block 16 is processed to form a single image of the colored sheet. According to various embodiments, the forming of the single image may be accomplished by a scan alignment module that utilizes overlapped pixels to accurately align the scan information (representative of the entire colored sheet, cylindrical-shaped portions thereof or helical-shaped portions thereof) into its proper relationship to form a rectangular image of the measured colored sheet. The resulting information comprises accurate color information representative of the colored sheet and may be utilized for quality control purposes. For example, the resulting information may be utilized to provide feedback to the automated ink control units, to various motor drives, and to a measuring head acquisition timebase to correct for any misalignment found in the overlapped pixel region. The resulting information may be stored in a memory.

According to various embodiments, the method may advance from block 18 to block 20, where the measuring equipment may retain the measured colored sheet for a period of time. During the period of time, for processes that dry back, the ink will generally continue to dry and the temperature of the colored sheet may be monitored. After the appropriate period of time, a second measurement of the colored sheet may be obtained. After another appropriate period of time, a third measurement of the colored sheet may be obtained, and soon. The information obtained by the addition measurements may be utilized to monitor ink dry back and more accurately predict the final dried color of the ink. The measurement information and the information concerning the predicted final dried color may be stored in a memory.

The prediction of the final dried color of the ink may be determined by a dry back module. According to various embodiments, the dry back module may fit the data from one or more of the multiple measurements to an exponential function and predict the final spectral or colorimetric value of each different colored area of the measured colored sheet. The dry back module may be configured to compensate for the fact that the colored sheet may be measured while the ink is still wet.

Figure 2:
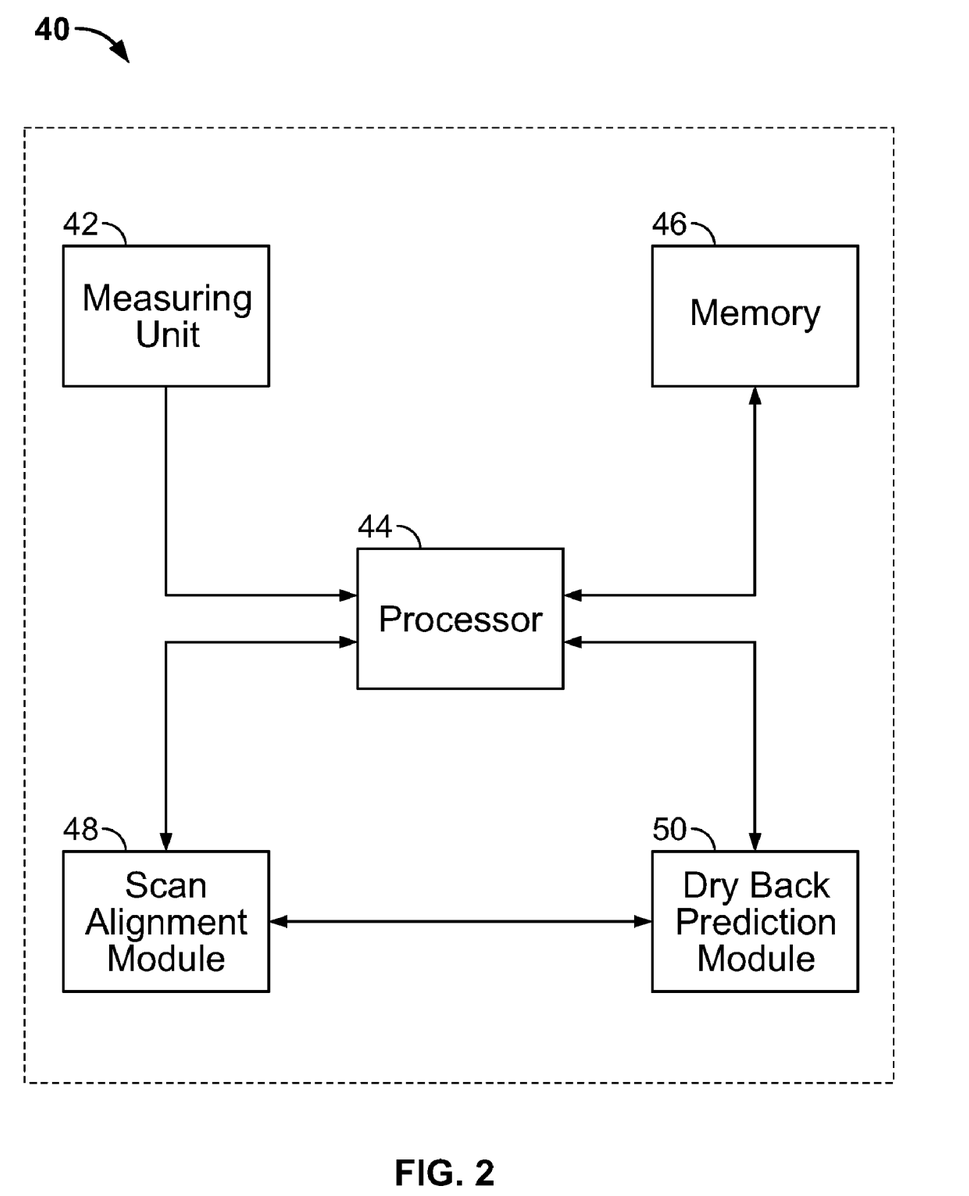
FIG. 2 illustrates various embodiments of a system for measuring a colored flexible material during a manufacturing process.

FIG. 2 illustrates various embodiments of a system 40 for measuring a colored flexible material during a manufacturing process. In general, one or more elements of the system 40 may perform the method 10 as described above.

The system 40 includes a measuring unit 42, a processor 44, a memory 46, a scan alignment module 48, and a dry back module 50. According to various embodiments, one or more of the processor 44, the memory 46, the scan alignment module 48, and the dry back module 50 may comprise a portion of the measuring unit 42. According to other embodiments, one or more of the processor 44, the memory 46, the scan alignment module 48, and the dry back module 50 may be separate and apart from the measuring unit 42. For example, as shown in FIG. 2, the processor 44 may be in wired or wireless communication with the measuring unit 42, and the memory 46, the scan alignment module 48, and the dry back module 50 may be in wired or wireless communication with the processor 44. According to other embodiments, some system components may communicate with other system components in a different manner.

The measuring unit 42 may be any measuring unit suitable for measuring spectral data of a colored flexible material during a manufacturing process. According to various embodiments, the measuring unit 42 may comprise a portion of a larger piece of manufacturing equipment such as, for example, a printing press. The memory 46 may be any type of memory suitable for storing data.

The scan alignment module 48 may be configured to accurately align scan information (representative of the entire colored sheet, cylindrical-shaped portions thereof, or helical-shaped portions thereof) to form an image of the colored flexible material. According to various embodiments, the scan alignment module 48 may also be configured to provide feedback to various subsystems/components of the manufacturing equipment.

The dry back module 50 may be configured to accurately predict the final dried color of a portion of the colored flexible material. The final color is representative of the final color of the ink, colorant, coating, etc. used in the production process. The dry back module 50 may also be configured to compensate for the fact that the flexible colored material may be measured while the ink, colorant, coating, etc. is still wet.

According to various embodiments, each of the modules 48, 50 may be implemented in a field programmable gate array. Alternatively, each of the modules 48,50 may be implemented as software applications, computer programs, etc. utilizing any suitable computer language (e.g., C, e++, Delphi, Java, JavaScript, Pen, Visual Basic, VBScript, etc.) and may be embodied permanently or temporarily in any type of machine, component, physical or virtual equipment, storage medium, or propagated signal capable of delivering instructions to a device. The software code may be stored as a series of instructions or commands on a computer-readable medium such that when the processor 44 reads the medium, the functions described herein are performed.

As used herein, the term "computer-readable medium" may include, for example, magnetic and optical memory devices such as diskettes, compact discs of both read-only and writeable varieties, optical disk drives, and hard disk drives. A computer-readable medium may also include memory storage that can be physical, virtual, permanent, temporary, semi-permanent and/or semi-temporary, A computer-readable medium may further include one or more propagated signals, and such propagated signals mayor may not be transmitted on one or more carrier waves.

Although the modules 48, 50 are shown in FIG. 2 as two separate modules, one skilled in the art will appreciate that the functionality of the modules 48, 50 may be combined into a single module. Also, although the modules 48, 50 are shown as being part of a common system 40, the modules 48, 50 may be installed on separate, distinct systems that are in wired or wireless communication with one another. For example, for embodiments where one or more of the modules 48, 50 are installed on separate distinct systems, the modules may be in communication with one another via a network (not shown). Such a network may include any type of delivery system including, but not limited to, a local area network (e.g., Ethernet), a wide area network (e.g. the Internet and/or World Wide Web), a telephone network (e.g., analog, digital, wired, wireless, PSTN, ISDN, GSM, GPRS, and/or xDSL), a packet-switched network, a radio network, a television network, a cable network, a satellite network, and/or any other wired or wireless communications network configured to carry data. Such a network may also include elements, such as, for example, intermediate nodes, proxy servers, routers, switches, and adapters configured to direct and/or deliver data.

From the foregoing, one skilled in the art will appreciate that the disclosed invention may include a synchronization subsystem to synchronize the motion of the drum and the measuring head. It may also keep a time base synchronized to the motors to control the exact acquisition time of the measuring head. The synchronization system may be configured to assure that the same number of measurements are made for each revolution of the drum. To accomplish this, a high accuracy encoder may be attached to the drum. Encoder subsystem electronics may generate a pulse for a predefined fraction of a degree of angular rotation. The fraction may represent, for example about $\frac{1}{200}^{th}$ of an inch at the surface of the drum. If the drum speed varies slightly, the encoder subsystem may assure that a constant number of measurements are made for each revolution of the drum. A similar technique may be used for the measuring head subsystem that moves the measuring head along the longitudinal axis of the drum. The motion of the measuring head may also be metered by the encoder subsystem. If the drum speed varies slightly, the encoder subsystem may vary the speed of the measuring head so that the measured helical-shaped area progresses across the drum surface at a predictable rate. The disclosed invention provides predictable and controllable delays between the exact time of manufacture and the time of measurement. The predictability enables accurate closed loop control, and the control allows for specialized measurements (e.g., sheet cool down, ink dry back prediction, etc.).

While several embodiments of the invention have been described, it should be apparent, however, that various modifications, alterations and adaptations to those embodiments may occur to persons skilled in the art with the attainment of some or all of the advantages of the disclosed invention. Therefore, this application is intended to cover all such modifications, alterations and adaptations without departing from the scope and spirit of the disclosed invention as defined by the appended claims.

What is claimed is:

1. A method for measuring a colored flexible material during a manufacturing process, the method comprising:
    automatically diverting the flexible material from a process path;
    placing the flexible material in contact with a rotatable drum;
    measuring spectral data of the flexible material as the drum rotates, wherein the measuring comprises scanning the flexible material with a line scanning detector having an array of detectors; and processing scan information to form a single image of the flexible material.

2. The method of claim 1, wherein placing the flexible material in contact with the rotatable drum comprises placing the flexible material in contact with a smooth black drum.

3. The method of claim 1, wherein measuring the spectral data comprises measuring a color bar on the flexible material.

4. The method of claim 1, wherein scanning the flexible material comprises scanning a portion of the flexible material.

5. The method of claim 4, wherein scanning the portion of the flexible material comprises scanning a helical-shaped portion.

6. The method of claim 4, wherein scanning the portion of the flexible material comprises scanning a cylindrical-shaped portion.

7. The method of claim 1, wherein scanning the flexible material comprises illuminating the flexible material with a switchable narrow band light source.

8. The method of claim 1, wherein scanning the flexible material comprises scanning the flexible material with a plurality of line scanning detectors.

9. The method of claim 8, wherein scanning the flexible material comprises illuminating the flexible material with a different narrow band light source for each line scanning detector.

10. The method of claim 8, wherein scanning the flexible material comprises illuminating the flexible material with white light.

11. The method of claim 1, wherein scanning the flexible material comprises:
    illuminating the flexible material with white light; passing light reflected from the flexible material through a dispersive element; and detecting the passed light a two-dimensional detector.

12. The method of claim 11, wherein passing the reflected light comprises passing the reflected light through a prism.

13. The method of claim 11, wherein passing the reflected light comprises passing the reflected light through a grating.

14. The method of claim 11, wherein passing the reflected light comprises passing the reflected light through a prism and a grating.

15. The method of claim 1, wherein scanning the flexible material comprises:
projecting a line of light onto the flexible material; and
detecting a line of pixels across the flexible material.

16. The method of claim 15, wherein: projecting the line of light comprises projecting a plurality of parallel lines of light; and detecting the line of pixels comprises detecting a plurality of parallel lines of pixels.

17. The method of claim 1, further comprising scanning the flexible material at Least one additional time.

18. The method of claim 1, further comprising predicting a final color of a portion of the flexible material.

19. A system for measuring a colored flexible material during a manufacturing process, the system comprising:
a measuring unit, including a rotatable drum, and one or more scanning detectors, each scanning detector having a measuring head; and
a scan alignment module for aligning scan information to form an image of the colored flexible material.

20. The system of claim 19, further comprising a dry back module for predicting a final dried color of a portion of the flexible material.

* * * * *